United States Patent [19]

Backman

[11] Patent Number: 5,169,768
[45] Date of Patent: Dec. 8, 1992

[54] METHOD OF BIOSYNTHESIS OF PHENYLALANINE

[75] Inventor: Keith C. Backman, Bedford, Mass.

[73] Assignees: BioTechnica International, Inc., Cambridge, Mass.; H.J. Heinz Company, Pittsburgh, Pa.

[21] Appl. No.: 401,493

[22] Filed: Aug. 28, 1989

Related U.S. Application Data

[63] Continuation of Ser. No. 860,543, May 7, 1986, abandoned, which is a continuation-in-part of Ser. No. 539,981, Oct. 7, 1983, abandoned.

[51] Int. Cl.$^5$ .................. C12P 13/22; C12N 1/21
[52] U.S. Cl. .................. 435/108; 435/252.33
[58] Field of Search .............. 536/27; 435/691, 71.2, 435/91, 172.3, 320.1, 108, 110, 113, 115, 116, 848, 252.33; 935/6, 9, 22, 29, 50, 60, 61, 66, 72, 73

[56] References Cited

U.S. PATENT DOCUMENTS

| | | | |
|---|---|---|---|
| 4,499,188 | 2/1985 | Konrad et al. | 435/69.51 |
| 4,681,852 | 7/1987 | Tribe | 435/108 |
| 4,743,546 | 5/1988 | Backman et al. | 935/14 X |

FOREIGN PATENT DOCUMENTS 0331145  9/1989  European Pat. Off. .

OTHER PUBLICATIONS

Sugimoto, et al., *App. Microbiol Biotechnol*, vol. 22, pp. 336-342, Sep., 1985.
Kornberg (1966) Biochem. J. 99:1-11.
Krulwich et al. (1976) *J. Bacteriol.* 127:179-83.
Gowrishankar, J. et al. *J. Bacteriol.*, 150(3): 1130-1137, (1982).
DeBoer, H. A. et al. *Promoters, Structure and Function* Rodriguez et al. (eds), 462-481, (1982).
Backman, K. et al. *Proc. Natl. Acad. Sci*, 78(b): 3743-3747 (1981).
Roberts et al. *Proc. Natl. Acad. Sci.* 76(2): 760-764 (1979).

*Primary Examiner*—Richard A. Schwartz
*Assistant Examiner*—Nancy T. Vogel

[57] ABSTRACT

A method of controlling of cell mass by starving cells that are ppc$^-$ and pc$^-$ for tricarboxylic acid cycle (TAC) intermediates, while fermenting a product compound. The cells are adapted to enable or enhance conversion of a raw material to the product via a bioconversion pathway that does not include any TAC intermediates, and preferably they are either conditionally or permanently incapable of producing a net increase in TAC intermediates via any anaplerotic pathways. First the cells are cultured to the desired cell mass under growth medium conditions characterized by the presence of at least one TAC intermediate, or by the presence of a compound that the cells can convert to a TAC intermediate via an anaplerotic pathway under the conditions present in the growth medium. In that way the medium provides the cell enough TAC intermediates to support growth. When the desired cell density has been reached, the cells are cultured under product-production medium conditions in which the cell does not receive adequate TAC intermediates to support growth, because the medium lacks TAC intermediates as well as compounds that they all can convert to TAC intermediate via an anapleortic pathway.

8 Claims, 1 Drawing Sheet

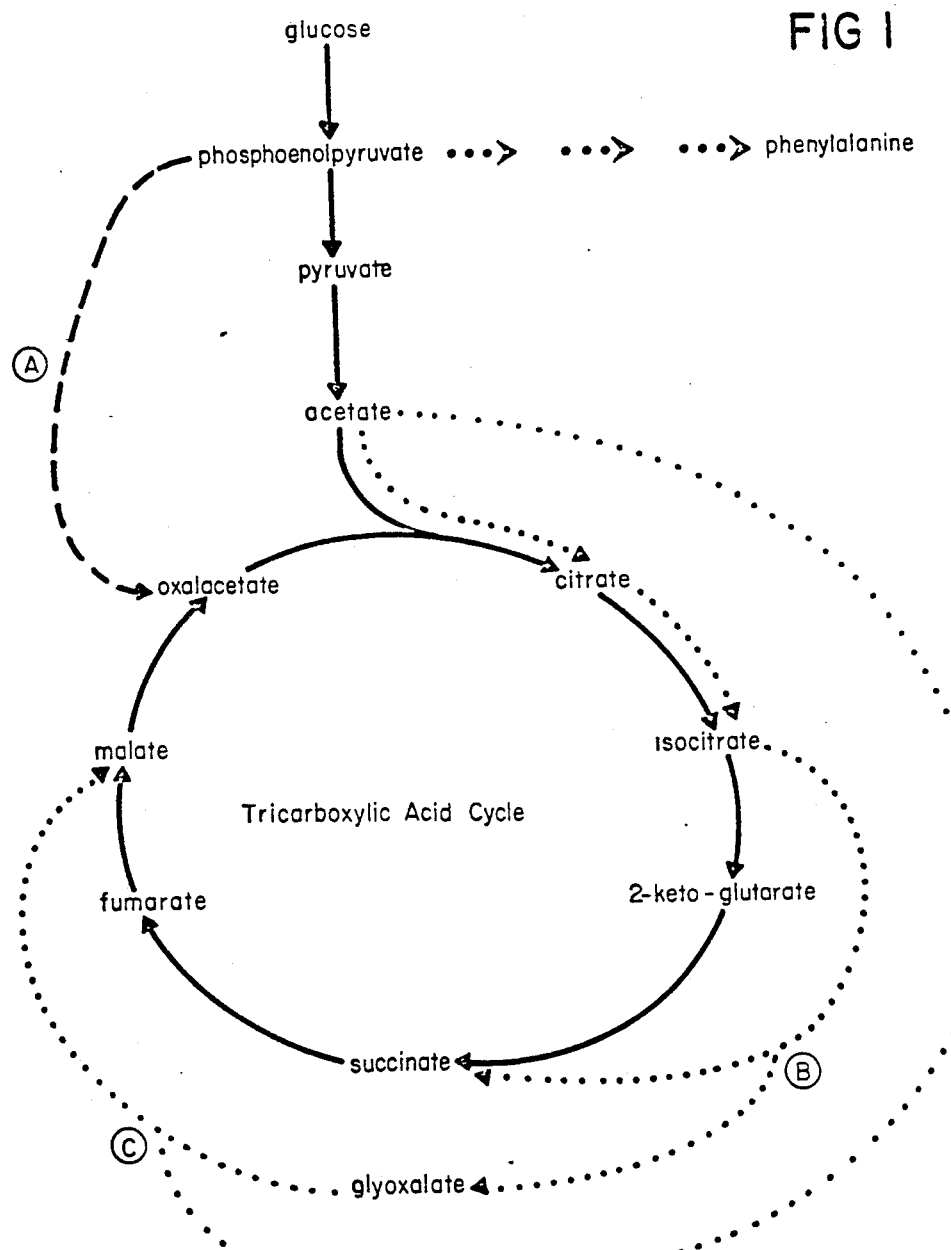

METHOD OF BIOSYNTHESIS OF PHENYLALANINE

This is a continuation of application Ser. No. 06/860,543, filed on May 7, 1986, now abandoned, which is a continuation-in-part of application U.S. Ser. No. 539,981 filed Oct. 7, 1983, now abandoned, which is hereby incorporated by reference.

BACKGROUND OF THE INVENTION

This invention relates to producing a desired compound and to cells used in such production.

In conducting fermentation, the cell mass should be adequate to convert raw material into product, but there are conflicting considerations. For example, in some situations, product yields may be reduced if raw material is squandered to support growth of the cell mass substantially in excess of the amount needed for a reasonable rate of raw material conversion.

FIG. 1 shows the tricarboxylic acid cycle (TAC), by which cells derive energy from carbohydrates quasi-catalytically. Specifically, in the TAC, a highly oxidized four-carbon intermediate is fused to a less oxidized two-carbon intermediate; then two relatively highly oxidized single-carbon molecules (carbon dioxide) are severed, leaving a less oxidized four-carbon molecule. Useful energy is derived by oxidizing that less-oxidized four-carbon molecule back to the starting point, oxalacetate.

The net effect of the TAC is the oxidation of acetate to carbon dioxide to produce energy. There is not net consumption of any of the TAC intermediates in this process. The term TAC intermediates means four-, five-, or six-carbon compounds in the TAC: citrate, isocitrate, α-keto-glutarate, succinate, fumarate, malate, and oxalacetate.

The TAC has another important function in the cell, however. It provides a pool of biosynthetic precursors for a variety of important cellular components, including amino acids and nucleic acids. Thus, while the TAC intermediates are not consumed in the above-described catabolic cycle, these intermediates are siphoned off, particularly during cell growth, to form various cellular components, and a mechanism for replacing these intermediates is needed to support cell growth. Anaplerotic pathways are bioconversion pathways by which the cell effects a net increase in TAC intermediates, e.g. by converting a compound outside the TAC into a TAC intermediate without consuming an equal number of TAC intermediate. For example, the glyoxalate shunt, which nets malate from acetate, is one anaplerotic pathway. The conversion of phosphoenolpyruvate or pyruvate to oxalacetate is another.

Kornberg (1966) *Biochem. J.* 99:1-11 describes cells which are ppc−, meaning they are defective in their ability to carboxylate phosphoenolpyruvate to form oxalacetate, thus preventing the cells from replacing TAC intermediates by that mechanism. The cells are referred to as ppc−, because the enzyme involved in the carboxylation is phosphoenolpyruvate-carboxylase. Some microorganisms are capable of carboxylating pyruvate with pyruvate carboxylase. In this application, the terms "ppc−" and "pc−" refer to cells that are incapable of carboxylation of phosphoenolpyruvate and pyruvate, respectively, to replenish TAC intermediates.

SUMMARY OF THE INVENTION

I have discovered that cells with certain metabolic deficiencies enable enhanced production of certain product compounds. The metabolic deficiencies are that the cells are ppc−, and they are preferably at least conditionally incapable of replacing TAC intermediates via the glyoxalate shunt. The products are those produced via a bioconversion pathway that is free from any tricarboxylic acid cycle (TAC) intermediates.

In preferred embodiments, the product is one of the aromatic amino acids (phenylalanine, tyrosine, or tryptophan) or it is glycine, serine, alanine, or cysteine. Also preferably, production is performed under conditions which effectively prevent TAC intermediate replacement.

It is particularly surprising that ppc− and pc− cells produce any specific product (e.g., aromatic amino acids) at enhanced levels, because such cells accumulate acetate when TAC intermediate replacement is shut off, which can be detrimental to cell processes, and there is no indication that such accumulation can be beneficial in producing any specific product.

Also in preferred embodiments, the method is used to control cell mass by starving the cell for tricarboxylic acid cycle (TAC) intermediates while fermenting a product compound. The cells are adapted to enable or enhance conversion of a raw material to the product via a bioconversion pathway that does not include any TAC intermediates.

In this embodiment, the cells first are cultured to the desired cell mass under growth medium conditions characterized by the presence of at least one TAC intermediate, or by the presence of a compound that the cells can convert to a TAC intermediate either directly or via an anaplerotic pathway under the conditions present in the growth medium. In that way the growth medium provides the cell enough TAC intermediates to support growth. When the desired cell density has been reached, the cells are cultured under product-production medium conditions in which the cell does not receive adequate TAC intermediates to support growth, because the medium lacks TAC intermediates as well as compounds that the cells can convert to TAC intermediate either directly or via an anaplerotic pathway under the product-production medium conditions.

In preferred embodiments, the cells are conditionally or permanently incapable of the two specific anaplerotic pathways described above. For example, the conversion of pyruvate or phosphoenolpyruvate to oxalacetate may be permanently disabled, while the glyoxalate shunt is inhibited in the presence of a substance such as glucose. Most preferably, the growth medium includes a TAC intermediate or a compound the cells can convert directly to a TAC intermediate, e.g., aspartic acid and/or glutamic acid, and glucose, which provides a source of energy via the glycolytic pathway; the TAC intermediate enables growth even though the cells are inhibited by glucose from TAC replacement via the glyoxalate shunt. In such methods, the product compound preferably is not one that is produced in the glycolytic pathway—i.e., products in the Embden-Meyerhof pathway sequence: glucose; glucose-6-phosphate; fructose-6-phosphate; fructose-1,6-diphosphate; dihydroxyacetone-phosphate; glyceraldehyde-3-phosphate; 1-3-diphosphoglycerate; 3-phosphoglycerate; 2-phosphoglycerate; phosphoenolpyruvate (PEP); pyruvate; acetaldehyde; and acetate. Also preferably, the cells are microbial cells from a genus such as Bacillus, Streptomyces, Escherichia, Klebsiella, Salmonella, or Saccharomyces, and the cells comprise a cloning vector and other engineered improvements to enhance their product production, such as a vector comprising DNA coding for an enzyme in the product-production pathway.

The invention also features ppc⁻ cells that have been engineered to enhance product production, e.g., conversion of chorismate to phenylalanine or another aromatic amino acid. Preferably the cell comprises a vector comprising DNA encoding an enzyme that catalyzes a reaction in the bioconversion pathway. Also preferably, the cell is a member of a genus Bacillus, Streptomyces, Escherichia, Klebsiella, Salmonella, and Saccharomyces.

Thus the invention provides a method of significantly enhanced production levels using cells adapted from ppc⁻ cells. In addition, the invention allows a convenient method of controlling the extent of the cell mass by controlling the availability of TAC intermediates. The method is not dependent on limiting any nutrient that is required for effecting the conversion of raw material to end product, and the method channels the cell's metabolism away from growth pathways, thereby increasing the efficiency of conversion of raw material to end product.

Other features and advantages of the invention will be apparent from the following description of the preferred embodiments and from the claims.

DESCRIPTION OF THE PREFERRED EMBODIMENT

I first briefly describe the drawings of the preferred embodiment.

I. DRAWINGS

FIG. 1 is a flow diagram showing various bioconversion pathways used in growth and fermentation.

II. THE MICROBIAL CELLS

In the preferred embodiment, the metabolic characteristics of the cells are illustrated in FIG. 1. In FIG. 1, cells derive energy from carbohydrates by degradation through a variety of pathways to PEP, which enters the tricarboxylic acid pathway. As used in this application, carbohydrates means glucose, other saccharides, and polysaccharides which the cell can hydrolyze to saccharides. The TAC includes a catabolic route (shown in solid line in FIG. 1), which produces energy using the four-carbon intermediates quasi-catalytically: i.e., a highly oxidized four-carbon intermediate is fused to a less oxidized two-carbon intermediate; then two relatively highly oxidized one-carbon molecules (carbon dioxide) are severed leaving a less oxidized four-carbon molecule. Useful energy is derived by oxidizing that four-carbon molecule back to the starting point; i.e., oxalacetate. The net effect of this catabolic portion of the TAC is production of energy and carbon dioxide with a net loss of acetate. There is no net consumption or creation of four-carbon TAC intermediates.

Pathways for replacing TAC intermediates are known as anaplerotic (filling-up) pathways. In one such pathway (dashes in FIG. 1), PEP is converted to oxalacetate via the enzyme phosphoenolpyruvate carboxylase. In another such pathway (dots in FIG. 1), called the glyoxalate shunt of the TAC cycle, citrate is converted (via isocitrate) to succinate and glyoxalate by the enzyme isocitrate lyase. Acetate is combined with glyoxalate by the enzyme malate synthase to yield malate. The net result of the glyoxalate shunt is the replenishing of the TAC by a gain of a four-carbon TAC intermediate at the expense of two two-carbon molecules (acetate).

A cell that has lost its ability to replenish TAC intermediates from phosphoenolpyruvate can nevertheless grow on acetate, because TAC intermediates are replenished via the glyoxylate shunt. However, the glyoxylate shunt is inhibited by products of the glycolytic pathway upstream from acetate. Thus cells which are capable of growth on acetate alone are inhibited from growth by the addition of glucose. [Kornberg (1966) Biochem. J. 99:1-11; Krulwich et al. (1976) J. Bacteriol. 127:179-183].

It is possible to develop cell strains whose growth on a non-carbohydrate such as acetate is inhibited by glycolytic pathway substances produced from carbohydrates, and which nevertheless retain their viability and their ability to produce a desired fermentation product in the presence of carbohydrates and/or acetate. As explained below, growth of such cells may be readily controlled, e.g. in a fermentation process. The products thus produced include compounds which: 1) preferably are not produced in the glycolytic pathway; and 2) are produced by a pathway which does not produce a net increase of a TAC intermediate; and 3) are biosynthetically derived solely from glycolytic intermediates.

The cells may be formed by modifying a parent cell to enable (or enhance the effectiveness of) a pathway for forming those product compounds, and modifying parent cells to impair their ability to form phosphoenolpyruvate carboxylase, and thus their ability to convert PEP to oxalacetate.

Suitable cell lines include those belonging to the following genera: Bacillus, Streptomyces, Escherichia, Klebsiella, Salmonella, and Saccharomyces, and particularly strains derived from wild-type strains capable of converting carbohydrates to TAC intermediates. A particularly preferred species is E. coli, and strains thereof described below which are derived from the K12 strain YMC9, and which lack the ability to synthesize phosphoenolpyruvate carboxylase (PPC), an enzyme necessary for conversion of glucose to TAC intermediates, by virtue of lesions in the ppc gene.

A. KB260

Strain KB260, a strain which demonstrates control of cell-mass growth but has not been specifically modified to enhance production of a desired product compound, is constructed as follows. Strain YMC9 (ATCC accession No. 33927) is mutagenized with the mud(amp lac)1 random insertional mutator element according to the procedure of Casadaban and Cohen (Casadaban, M. J., and Cohen, S. N. Proceedings of the National Academy of Sciences 76:4530-4533 [1979]). Cells which have been mutated are selected by growth in the presence of ampicillin, since acquisition of the mutator element results in resistance to β-lactam antibiotics. A large pool of random mutants is selectively enriched for mutants unable to synthesize arginine by growing the pooled mutants in M9 minimal salts supplemented with 2 mg/ml glucose with 1 μg/ml thiamine and 40 μg/ml L-arginine at 30° C. until the culture is growing logarithmically, next collecting and washing the cells by filtration, resuspending the cells in M9 minimal salts with 2 mg/ml glucose and 1 μg/ml thiamine, incubating the cells at 30° C. for 1 to 1.5 hours, adding D-cycloserine (final concentration: 0.002 M), and collecting the viable cells which remain after lysis of the culture. Among these cells are mutants of YMC9 which cannot grow in the absence of exogenous arginine (or a biosynthetic precursor of arginine). Typical of such mutants is strain KB243 which is capable of growth when the medium is supplemented with arginine, or with either ornithine or citrulline, which are precursors of arginine.

Strain KB243 is plated on agar plates containing M9 salts, 2 mg/ml glucose, 1 μg/ml thiamine, 40 μg/ml L-arginine, and 0.5 mg/ml succinate and incubated at 42° C. This results in the death of most cells on the plate because of lethal functions on the mud(amp lac)1 element. Among the surviving bacteria are deletion mutants which had lost portions of the mud(amp lac)1 element and surrounding DNA. An exmaple of such a strain is KB244, which has lost genetic information for resistance to β-lactam antibiotics and is incapable of growth when provided with ornithine or citrulline instead of arginine. This last property identifies the lesions in the arginine biosynthetic pathway as falling in the genes of the argECBH cluster, which is linked to the ppc gene on the E. coli chromosome (Bachmann, B. J. Microbiological Reviews 47:180–230 [1983]).

Strain KB244 is transduced to arginine prototrophy with P1 bacteriophage grown on E. coli strain DL10 (LeMaster, D. M. and Cronan, Jr., J. F. Journal of Biological Chemistry 257:1224–1230 [1982]) which has an unmutated argECBH cluster but carries a mutation in the ppc gene. Isolates are examined for growth on M9 minimal salts plus 2 mg/ml glucose and 1 μg/ml thiamine, plus or minus 0.5 mg/ml succinate. Strains which acquire a ppc$^-$ allele are unable to grow without the succinate or some other source of TAC intermediates. Typical of the ppc$^-$ transductants obtained is KB260.

The mutation in the KB260 gene responsible for affecting phosphoenolpyruvate carboxylase (PPC) synthesis is a point mutation, and, therefore, there is the possibility of reversion, resulting in acquisition of the ability to synthesize PPC. Other strains are described below in which the loss of PPC synthesis is attributable to a type of mutation that is less susceptible to reversion.

B. KB280 and KB285

Strains KB280 and KB285, which demonstrate control of cell-mass growth in a fermentation process, are constructed as follows. Strain YMC9 is mutagenized with the mud(amp lac)1 insertional mutator element, as above. A pool of mutated cells is enriched for ppc$^-$ mutants by growing them on M9 minimal salts with 2 mg/ml glucose, 1 μg/ml thiamine, and 0.5 mg/ml succinate at 30° C. until the culture is growing logarithmically, collecting and washing the cells by filtration, resuspending the cells in M9 minimal salts plus 2 mg/ml glucose, and 1 μg/ml thiamine, incubating the cells at 30° C. for 1 to 1.5 hours, adding D-cycloserine (final concentration: 0.002 M) and collecting the viable cells which remain after lysis of the culture. Among such cells are mutants which require exogenous succinate for growth in the presence of glucose. Typical of such strains are KB279 and KB284. Cells of each strain are plated on agar plates containing M9 salts, 2 mg/ml glucose, 1 μg/ml thiamine, 0.5 mg/ml succinate, and 40 μg/ml L-arginine and incubated at 42° C. Among survivors are bacteria which have lost portions of the mud-(amp lac)1 element and surrounding DNA. Such strains are no longer resistant to β-lactam antibiotics, and certain isolates have acquired a requirement for exogenous arginine for growth.

This property confirms that the lesions in KB279 and KB284 are in fact in the ppc gene. Isolates KB280 (from KB279) and KB285 (from KB284) are saved. Each has lost its progenitor's resistance to β-lactam antibiotics, but neither has acquired a defect in arginine biosynthesis. KB280 and KB285 have been deposited with the American Type Culture Collection and have accession numbers ATCC 39461 and ATCC 39463, respectively.

C. PLASMIDS ENABLING PHENYLALANINE PRODUCTION

Depending on the desired product and the capability of the parent cells, strains may require modification, such as by the addition of a plasmid with DNA coding for an enzyme catalyzing a reaction in the product fermentation pathway. For example, to produce L-phenylalanine (a component of a non-sugar sweetener useful in a wide variety of food products) the strains described above are transformed with a plasmid such as pKB663 or pKB702 described below.

i. pKB663

A fragment of DNA carrying the pheA gene of E. coli but not its associated promoter, operator, leader peptide, or attenuator is prepared from plasmid pKB45 (Zurawski, G., et al. Proceedings of the National Academy of Sciences 75:4271–4274 [1978]) by digestion with endonucleases StuI and BglII. Plasmid pKB430 is a derivative of pBR322 which carries a lactose operon promoter-operator abutting an endonuclease PvuII cleavage site. The pheA containing DNA fragment is cloned by standard techniques (Bolivar, F. and Backman, K. Methods in Enzymology, Vol. 68 [1980]) in pKB430 between the PvuII and BamHI cleavage sites, yielding pKB663. On pKB663, expression of pheA is directed by the lac promoter and is not regulated in response to accumulation of L-phenylalanine, as is the pheA gene when associated with its normal regulatory elements. pKB663 also carries a gene which determines resistance to β-lactam antibiotics such as ampicillin. Plasmid pKB663 is available from YMC9/pKB663 which is deposited with the American Type Culture Collection and has accession number ATCC 39462. See co-pending commonly owned application Backman, Method of Biosynthesis and Cells Therefor, Ser. No. 653,193, filed Sep. 24, 1984, which is hereby incorporated by reference.

ii. pKB702

Plasmid pKB702 is described in Backman et al., "Enzyme Deregulation" U.S. Ser. No. 06/860,541, filed May 7, 1986, now U.S. Pat. No. 4,753,883, which is commonly owned with this application and hereby incorporated by reference. pKB702 carries an altered pheA gene that determines a feedback insensitive chorismate mutase-prephenate dehydratase enzyme. Specifically, pKB702 is deleted for a region of the E. coli pheA gene between an internal NcoI site and the end of the gene. Plasmid pKB702 is deposited with the ATCC in E. coli K12 MM294 and has Accession No. 67068.

Strains YMC9, KB280, and KB285 are transformed with pKB663 or pKB702 (see Bolivar, F. and Backman, K. Methods in Enzymology, Vol. 68 [1980]) yielding YMC9/pKB663, KB280/pKB663, and KB285/pKB663, YMC9/pKB702, KB280/pKB702, and KB285/pKB702. In addition to enabling phenylalanine production, pKB663 and pKB702 each carry genes for resistance to ampicillin (both) and tetracycline (pKB702 only).

III Controlling Cell Mass and Product Production

Either one of two specific cell-mass control techniques can be used with any of the above ppc⁻ strains, such as KB260, KB280, and KB285 or derivates of those strains obtained by transformation with DNA supporting product production.

A. Growth on Succinate and Glucose

The strains described above are cultivated on a medium that contains a TAC intermediate, preferably succinate or a compound which can be directly converted to a TAC intermediate, such as glutamic acid or aspartic acid, and glucose. While the glucose inhibits TAC replacement via the glyoxalate shunt, the succinate provides sufficient TAC intermediate replacement to support cell growth. The glucose is useful to support other cell growth processes, and to supply energy via glycolysis. The amount of succinate provided is selected to achieve the desired cell mass. A supply of glucose is maintained by supplementing the medium or by including an excess of glucose initially. For example the glucose concentration in the growth medium should be maintained at about 1 mg/ml to 25 mg/ml. The initial succinate concentration should be about 0.1 mg/ml to 1.0 mg/ml for the above described strains of *E. coli*. Additional succinate may be added to the medium during growth to permit higher cell densities to be achieved.

Once the succinate is depleted, growth will stop, if the anaplerotic pathways are inhibited or disabled. For example, the above-described strains of *E. coli* will not grow in the presence of the above glucose concentrations, because the glyoxalate shunt is inhibited.

In one specific example, one of the above described strains can be inoculated into a culture containing 20 ml of M9 salts, about 4 mg/ml glucose, 1 µg/ml thiamine, and a determinate amount of succinate. The strain is incubated at about 37° C., and growth ensues. After a period of time that depends on the initial level of succinate in the medium, growth stops. Addition of more succinate at this point restores growth, thereby identifying insufficient TAC intermediates as the cause of growth limitation. In this kind of experiment, the ppc⁻ cells exhibit behavior that is entirely different from the ppc⁺ YMC9 parent strains; the latter will not cease growth due to succinate depletion from the medium so long as glucose is supplied, and growth continues until other factors exert control.

Cultures of KB285/pKB702 or YMC9/pKB702 are grown on the medium described in Table 1, below, with between 0.3 and 1.0 mg/ml succinate. During growth and at the end of growth, phenylalanine production is monitored. Both during growth, and significantly, after succinate limitation of the ppc⁻ culture, the productivity of phenylalanine is significantly enhanced in the ppc⁻ strain as compared to the ppc⁺ strain.

B. Growth on Acetate; Addition of Glucose

In an alternative method, growth is enabled by the inclusion of acetate in the growth medium, and the absence from that medium of glucose or other carbohydrates. Specifically, one of the ppc⁻ strains is cultivated on a carbohydrate-free medium. If carbohydrates are present initially, they will be metabolized to inhibiting compounds which will stop growth. Eventually, the carbohydrates and glycolytic intermediates may be depleted by various metabolic pathways, and growth can begin. Once desired cell mass is achieved a carbohydrate is added to inhibit continued cell growth by inhibiting the glyoxalate shunt, thus depriving the cell of its only source of replacement of TAC cycle intermediates needed for cell growth. The amount of carbohydrate added may depend in some measure largely on whether the carbohydrate serves solely as a generator of inhibiting substance, or whether it also serves as the raw material for production of the desired compound. About 2 to 4 mg/ml of glucose is satisfactory to inhibit cell growth. More glucose is added (either at the outset of the product formation phase or continuously during that phase) when glucose serves as the raw material for product synthesis in order to maintain enhanced raw material levels to drive biosynthetic pathway reactions.

As specifically related to the above-described strains of *E. coli*, strain KB260 is inoculated into a culture containing 20 ml of M9 salts, 4 mg/ml sodium acetate, 1 µg/ml thiamine and grown at 37° C. Culture turbidity is monitored with a Klett-Summerson Colorimeter. When the turbidity reaches 40–50 Klett units (green filter), glucose (final concentration: 4 mg/ml) is added to the KB260 culture, and culture turbidity of all cultures is monitored for another nineteen hours. The number of viable cells in the KB260 culture is also determined four hours and nineteen hours after the addition of glucose.

The growth rate of KB260 is like that of its parent YMC9 (ppc⁺) when grown entirely on acetate, but KB260 and YMC9 respond dramatically differently to the addition of glucose. YMC9 increases its growth rate and reaches a higher saturation density with glucose than either YMC9 or KB260 on acetate alone. KB260 in contrast, ceases accumulation of cell mass shortly after the addition of glucose, and fails to accumulate new cell mass over intermediate to long times. Unlike many other schemes in which an added substance halts cell growth, however, the addition of glucose to the KB260 culture does not significantly impair the viability of the cells.

Cultures of YMC9 and one of the above ppc⁻ strains including pKB663 are grown at 37° C. in 20 ml of M9 salts, as described above to a density of either 45 to 60 or 130 to 150 Klett units (green filter), at which time the culture is collected by filtration, the cells are resuspended in an equal volume of fresh medium, and glucose is added or maintained at a concentration of 4 mg/ml, and cell growth is controlled.

Incubation is continued at 37° C. for 10 to 15 hours, at which point culture density, cell viability, and L-phenylalanine content of the medium are determined. At this point, the productivity for phenylalanine of the ppc⁻ culture is superior to that of the ppc⁺ culture. Additional information concerning the method of modifying YMC9 and the method of culturing the modified cells to produce L-phenylalanine is described in my co-pending applications entitled Method Of Biosynthesis And Cells Therefor, U.S. Ser. No. 540,190, filed Oct. 7, 1983, now abandoned, and U.S. Ser. No. 653,193, filed Sep. 24, 1984, now issued as U.S. Pat. No. 4,839,286, which are hereby incorporated by reference.

OTHER EMBODIMENTS

Other embodiments are within the following claims. For example, the cells used may be microbial cells or cell tissue from multi-celled organisms. The cells may be permanently (rather than conditionally) disabled from TAC replacement by the glyoxalate shunt, in which case glucose is needed only as a source of energy (via glycolysis) and as a source of raw material for product production.

TABLE I

| In order of Addition: | Stock Solution Concentration g/l | Volume Stock Solution/Liter Final Medium #m/l |
|---|---|---|
| 1) NH$_4$Cl | 214 g/l | 50 |
| 2) Na$_2$ EDTA* | .65M | 30 |
| 3) ZnSO$_4$.7H$_2$O | 3 | 10 |
| 4) MnSO$_4$.H$_2$O | 3 | 10 |
| 5) NaMoO$_4$.2H$_2$O | 9 | 10 |
| 6) CuSO$_4$.5H$_2$O | 9.38 | 10 |
| 7) CoCl$_2$.6H$_2$O | 10 | 10 |
| 8) H$_3$BO$_3$ | 3 | 10 |
| 9) KI | 7 | 10 |
| 10) B1-Thiamine | 0.1% | 1 (made fresh each time) |
| 11) NiCl$_2$ | 5 | 10 |
| 12) Glucose | 50% | 10 |
| 13) NH$_4$+ Succinate** (optional) | 100 | 8 |
| 14) Tetracycline (optional) | 1 | 0.5 |
| 15) Na Ampicillin (optional) | 10 | 5 |
| 16) Tyrosine (optional) | 1 | 12 |
| 17) MgSO$_4$.7H$_2$O | 296 | 10 |
| 18) CaCl$_2$.2H$_2$O | 13 | 10 |
| 19) FeCl$_3$.6H$_2$O | 16 | 10 |
| 20) dH$_2$O.Sterile | — | Total Volume to 950 ml |
| 21) 1.6M K$_2$HPO$_4$ | | 50 ml |

TABLE I-continued

| In order of Addition: | Stock Solution Concentration g/l | Volume Stock Solution/Liter Final Medium #m/l |
|---|---|---|
| 0.4M KH$_2$PO$_4$ | | |

*218.53 grams of Na$_2$EDTA are added to 700 ml dH$_2$O. The flask is then put under a pH probe to monitor the pH of the solution while NaOH (50/50 μ/μ) is added. The EDTA will be soluble at ~ pH 9.2. When pH of the solution is ~ 8.5, the NaOH should be added slowly preferably with titration. The final pH should not exceed pH 10.2. When pH is attained, bring volume to 1 l. Autoclave 15', or filter sterilize in .2 μm Millipore filter.
**A 10% solution is required. Use NH$_4$OH to dissolve succinic acid. Bring pH up to 6.8–7.2. Bring solution to volume of 1 l. Filter sterilize using .2 μm Millipore filter.

I claim:
1. A method of biosynthesis of phenylalanine via a pathway that comprises conversion of a glycolytic pathway intermediate into said phenylalanine, said method comprising,
  providing ppc−, pc− E. coli cells,
  culturing said cells in a growth medium until the cells reach a density appropriate for the production of said phenylalanine,
  culturing said cells in a production medium substantially free from tricarboxylic acid intermediates, said cells being incapable, in said production medium, of replacing tricarboxylic acid intermediates via the glyoxylate shunt, and
  recovering said phenylalanine.
2. The method of claim 1 in which said ppc−, pc− cells have been genetically engineered to enhance biosynthesis of said phenylalanine.
3. The method of claim 1 in which said production medium comprises a compound capable of being metabolized by said cells to an inhibitor of isocitrate lyase.
4. The method of claim 1 in which said production medium comprises glucose.
5. The method of claim 1 in which said growth medium comprises a tricarboxylic acid cycle intermediate.
6. The method of claim 1 in which said growth medium comprises acetate and is free from inhibitors of isocitrate lyase.
7. The method of claim 1 in which said production medium is formed by steps comprising adding glucose to said growth medium.
8. A ppc−, pc− E. coli cell transformed with an expression vehicle for expressing DNA encoding an enzyme catalyzing a step in the biosynthesis of phenylalanine from a glycolytic pathway intermediate.

* * * * *